(12) United States Patent  (10) Patent No.: US 8,519,151 B2
Gribkov et al.  (45) Date of Patent: *Aug. 27, 2013

(54) PROCESS FOR THE PREPARATION OF PYRAZOLE CARBOXYLIC ACID AMIDES

(75) Inventors: Denis Gribkov, Munchwilen (CH); Remo Stohler, Monthey (CH); Thomas Vettiger, Munchwilen (CH); Michael Rommel, Munchwilen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/642,393
(22) PCT Filed: Apr. 14, 2011
(86) PCT No.: PCT/EP2011/055872
§ 371 (c)(1),
(2), (4) Date: Oct. 19, 2012
(87) PCT Pub. No.: WO2011/131546
PCT Pub. Date: Oct. 27, 2011

(65) Prior Publication Data
US 2013/0035495 A1  Feb. 7, 2013

(30) Foreign Application Priority Data
Apr. 20, 2010 (EP) ..................... 10160437

(51) Int. Cl.
C07C 25/18 (2006.01)
(52) U.S. Cl.
USPC ....................... 548/374.1; 570/183
(58) Field of Classification Search
USPC ....................... 548/374.1; 570/183
See application file for complete search history.

(56) References Cited

FOREIGN PATENT DOCUMENTS
WO 2007/048556 5/2007
WO 2007/124907 11/2007

OTHER PUBLICATIONS

International Search Report, International Application No. PCT/EP2011/055872, completion date: Jun. 14, 2011.

*Primary Examiner* — Samantha Shterengarts
(74) *Attorney, Agent, or Firm* — R. Kody Jones

(57) ABSTRACT

The invention relates to a process for the preparation of formula (I) which process comprises a) reacting a compound of formula (II), wherein X is chloro or bromo, with an organometallic species to (III), wherein X is chloro or bromo; reacting the halobenzyne with a fulvene (IV), to a compound of formula (V) wherein X is chloro or bromo; b) hydrogenating V in the presence of a suitable metal catalyst to a compound of formula (VI) wherein X is chloro or bromo; and either c1) reacting the compound of formula VI with NH3 in the presence of a catalyst comprising palladium and at least one ligand to the compound of formula (VII); and d) reacting the compound of formula VII in the presence of a base with a compound of formula (VIII), to the compound of formula I; or c2 reacting the compound of formula (VI) in the presence of a copper catalyst and a ligand with the compound of formula (VIIIa), to the compound of formula (I).

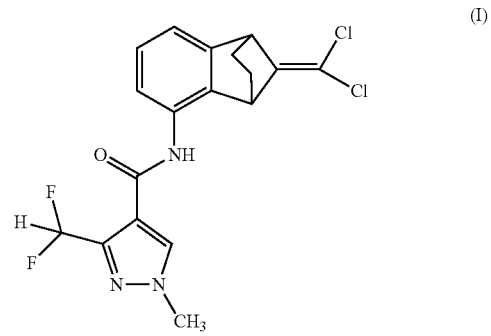

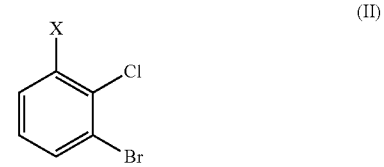

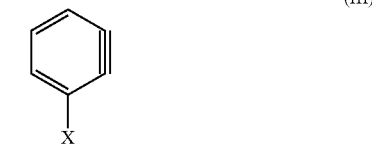

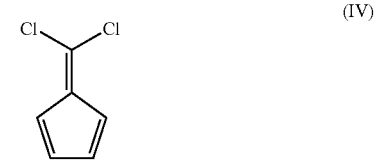

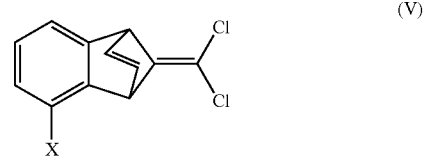

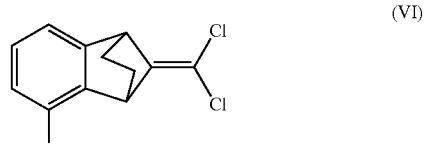

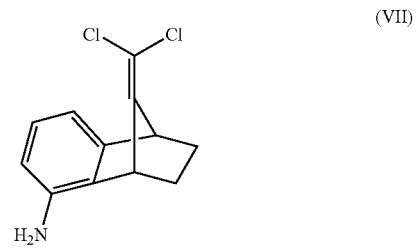

-continued
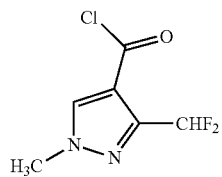
(VIII)
-continued
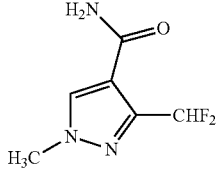
(VIIIa)
5 Claims, No Drawings

PROCESS FOR THE PREPARATION OF PYRAZOLE CARBOXYLIC ACID AMIDES

This application is a 371 of International Application No. PCT/EP2011/055872 filed Apr. 14, 2011, which claims priority to EP 10160437.9 filed Apr. 20, 2010, the contents of which are incorporated herein by reference.

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide and to novel intermediates useful for this process.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described for example in WO 2007/048556.

The preparation of 3-difluoromethyl-1-methyl-1H-pyrazole-4-carboxylic acid (9-dichloromethylene-1,2,3,4-tetrahydro-1,4-methano-naphthalen-5-yl)-amide is known from WO 2007/048556. Said compound can be prepared according to schemes 1 and 4 by a) reacting the compound of formula A

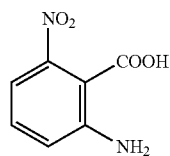

(A)

in the presence of an alkyl nitrite with a compound of formula B

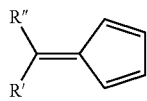

(B)

wherein R' and R" are e.g. $C_1$-$C_4$ alkyl, to a compound of formula C

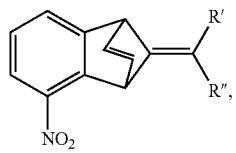

(C)

b) hydrogenating the compound of formula C in the presence of a suitable metal catalyst to a compound of formula D

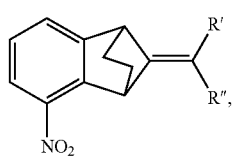

(D)

c) ozonising the compound of formula D and subsequent treatment with a reducing agent to a compound of formula E

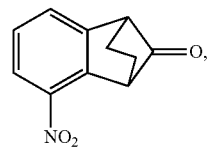

(E)

d) reacting the compound of formula E in the presence of triphenylphosphane/carbon tetrachloride to 2,9-dichloromethylidene-5-nitro-benzonorbornene of formula F

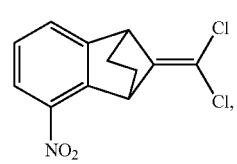

(F)

e) hydrogenating the compound of formula F in the presence of a metal catalyst to 2,9-dichloromethylidene-5-amino-benzonorbornene of formula G

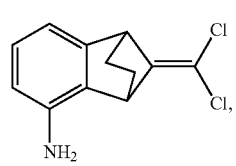

(G)

f) and reacting the compound of formula G with a compound of formula H

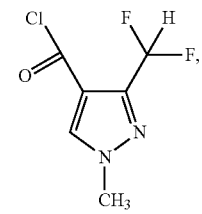

(H)

to 3-difluoromethyl-1-methyl-1H-pyrazole-4-carboxylic acid (9-dichloromethylene-1,2,3,4-tetrahydro-1,4-methano-naphthalen-5-yl)-amide.

A significant disadvantage of this prior art process is the ozonolysis reaction which is difficult to handle in large scale. Further, the large number of reaction steps reduces the overall yield of the process and increases the manufacturing costs. Said disadvantages make this process uneconomical and especially unsuitable for a large-scale production.

The aim of the present invention is therefore to provide a novel process for the production of 3-difluoromethyl-1-methyl-1H-pyrazole-4-carboxylic acid (9-dichloromethylene-1,2,3,4-tetrahydro-1,4-methano-naphthalen-5-yl)-amide that avoids the disadvantages of the known process and makes it possible to prepare 3-difluoromethyl-1-methyl-1H-pyrazole-4-carboxylic acid (9-dichloromethylene-1,2,3,4-tetrahydro-1,4-methano-naphthalen-5-yl)-amide in high yields and good quality in an economically advantageous way.

Thus, according to the present invention, there is provided a process for the preparation of the compound of formula I

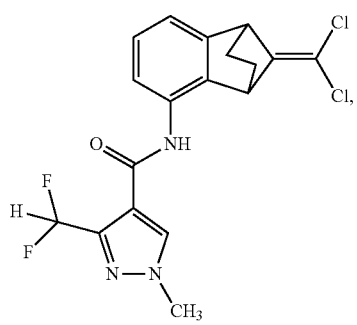 (I)

which process comprises
a) reacting a compound of formula II

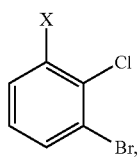 (II)

wherein X is chloro or bromo, with an organometallic species such as a $C_{1-6}$ alkyl- or phenyllithium or a $C_{1-6}$ alkyl- or a phenylmagnesium halide in an inert atmosphere to a halobenzyne of formula III

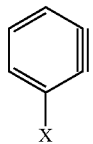 (III)

wherein X is chloro or bromo; reacting the halobenzyne of formula III so formed with a fulvene of formula IV

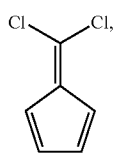 (IV)

to a compound of formula V

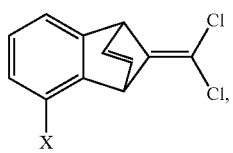 (V)

wherein X is chloro or bromo;

b) hydrogenating the compound of formula V in the presence of a suitable metal catalyst to a compound of formula VI

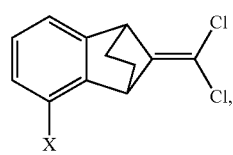 (VI)

wherein X is chloro or bromo; and either
c1) reacting the compound of formula VI with $NH_3$ in the presence of a catalyst comprising palladium and at least one ligand to the compound of formula VII

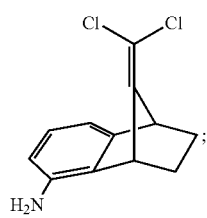 (VII)

and d) reacting the compound of formula VII in the presence of a base with a compound of formula VIII

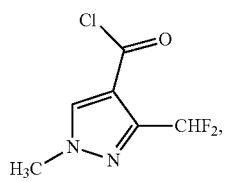 (VIII)

to the compound of formula I; or
c2) reacting the compound of formula VI

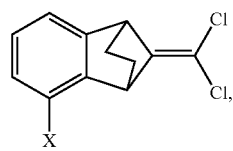 (VI)

wherein X is chloro or bromo, preferably bromo; in the presence of a solvent, a base, a copper catalyst and at least one ligand with the compound of formula VIIIa

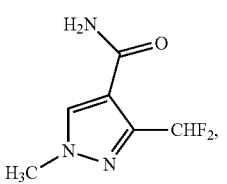 (VIIIa)

to the compound of formula I.

Reaction Step a):

The compound of formula II, wherein X is bromo, is known and disclosed, for example, in Recueil des Travaux Chimiques des Pays-Bas, 81, 365 (1962). The compound of formula II, wherein X is chloro or bromo, is disclosed, for example in WO 2008/049507. 1-bromo-2,3-dichloro-benzene may be prepared by the so-called Sandmeyer reaction from 2,3-dichloro-aniline. Such Sandmeyer reactions can be performed either by using an organic nitrite ester, such as tert-butyl nitrite or iso-pentyl nitrite, in an organic solvent, such as acetonitrile, in the presence of cupric bromide as brominating agent (as described in Journal of Organic Chemistry, 1977, 42, 2426-31) or by a two-step reaction involving diazotation in an acidic aqueous reaction media at temperatures of 0° C. to 15° C. using inorganic nitrite and then adding the reaction mixture to cuprous bromide solution (as described in Recueil des Travaux Chimiques des Pays-Bas et de la Belgique, 1932, 51, 98-113 and JP-6-2114-921).

6,6-Dichloro-fulvene of formula IV (RN 35310-97-5) is described in Chemical Communications, 20 (1971), 1293-1294.

The compound of formula V is novel, is especially developed for the process according to the invention and therefore constitutes a further object of the invention.

The reaction can be performed at temperatures from −78 to 20° C., preferably at −20° C.

The reaction is performed under semi-batch or continuous flow conditions, preferentially under semi-batch conditions.

As organometallic species, aryl- and alkyllithium compounds are used to perform the lithium halogen exchange, for example phenyllithium, methyl-lithium or n-butyl-lithium, preferably n-butyl-lithium.

Aprotic solvents are used as solvents, preferentially hydrocarbons like toluene.

Dosage of both the alkyllithium and the trihalogenebenzene to a solution of dichlorofulvene in a solvent over 15 to 180 minutes is preferred whereas also the dosage of the alkyllithium to a mixture of the trihalogenebenzene and the compound of formula IV in a solvent can be performed. Dosage of the alkyllithium and the compound of formula IV to a solution of the trihalogenebenzene in a solvent is also possible.

Complete conversion is usually achieved 15 to 180 minutes after completion of the addition of the corresponding reagents.

Reaction Step b):

The compound of formula VI can be prepared by the selective reduction of the non-chlorinated double bond using Raney Nickel (or Rh, Pd, Ir, Pt, Co and Fe catalysts either supported on a carrier or in combination with a ligand). The reaction can be performed under atmospheric or at elevated hydrogen pressure, preferentially under atmospheric pressure.

The reaction can be performed at ambient or elevated temperature, preferentially at ambient temperature, in particular from 20 to 25° C.

The reaction is performed in solvents which are inert towards Raney Nickel. A preferred solvent is ethyl acetate.

The compound of formula VI is novel, is especially developed for the process according to the invention and therefore constitutes a further object of the invention.

Reaction Step c1):

From the two process variants step c1) to step d) and step c2), the variant step c1) to d) is preferred. The catalyst which comprises palladium and at least one ligand used in the process will generally be formed from a palladium precursor and at least one suitable ligand. Where the process is carried out in a solvent, the complex will normally be soluble in the solvent.

In the context of this process palladium complexes expressly include those consisting of cyclic organic palladium compounds ("palladacycles") and secondary phosphane ligands.

The palladium complex may be used as a robust, preformed species or may be formed in situ. Typically it is made by reacting a palladium precursor with at least one suitable ligand. In the case of incomplete transformations, residual amounts of the palladium precursor or ligand may be present undissolved in the reaction mixture.

Useful palladium precursors may be chosen from palladium acetate, palladium chloride, palladium chloride solution, palladium$_2$-(dibenzylidene acetone)$_3$ or palladium-(dibenzylidene acetone)$_2$, palladium-tetrakis (triphenylphosphane), palladium/carbon, palladium dichloro-bis(benzonitrile), palladium-(tris-tert-butylphosphane)$_2$ or a mixture of palladium$_2$-(dibenzylidene acetone)$_3$ and palladium-(tris-t-butylphosphane)$_2$.

Useful ligands are, for example, tertiary phosphane ligands, N-heterocyclic carbene ligands and phosphanic acid ligands. Tertiary phosphane ligands are generally of two types: monodentate and bidentate ligands. A monodentate ligand may occupy one palladium coordination site while a bidentate ligand occupies two coordination sites and hence is able to chelate the palladium species.

The following are examples of tertiary phosphane, N-heterocyclic carbene and phosphanic acid ligands and a palladacycle with a secondary phosphane ligand.

(A) Monodentate phosphane ligands:

Tri-tert-butylphosphane, tri-tert-butylphosphonium tetrafluoroborate ("P(tBu)$_3$HBF$_4$"), tris-ortho-tolylphosphane ("P(oTol)$_3$"), tris-cyclohexylphosphane ("P(Cy)$_3$"), 2-di-tert-butyl-phosphano-1,1'-bisphenyl ("P(tBu)$_2$BiPh"), 2-di-cyclohexyl-phosphano-1,1'-bisphenyl ("P(Cy)$_2$BiPh"), 2-di-cyclohexylphosphano-2',4',6'-tri-isopropyl-1,1'-bisphenyl ("x-Phos"), and tert-butyl-di-1-adamantyl-phosphane ("P(tBu)(Adam)$_2$").

More information about monodentate phosphane ligands can be found in US-2004-0171833.

(B) Bidentate tertiary phosphane ligands:

(B1) Biphosphane ligands:

(B1.1) Ferrocenyl-Biphosphane ligands ("Josiphos" ligands):

1,1'-bis(diphenylphosphano)ferrocene (dppf), 1,1'-bis(di-tert-butylphosphano)-ferrocene, (R)-(−)-1-[(S)-2-(bis(4-trifluoromethylphenyl)phosphano)ferrocenyl]ethyl-di-tert-butyl-phosphane, (R)-(−)-1-[(S)-2-(di(3,5-bis-trifluoromethylphenyl)phosphano)ferrocenyl]ethyl-dicyclohexylphosphane, (R)-(−)-1-[(S)-2-(di(3,5-bis-trifluoromethylphenyl)phosphano)-ferrocenyl]ethyldi(3,5-dimethylphenyl)phosphane, (R)-(−)-1-[(S)-2-(dicyclohexylphosphano)-ferrocenyl]ethyldi-tert-butylphosphane, (R)-(−)-1-[(S)-2-(dicyclohexylphosphano)ferrocenyl]-ethyldicyclohexylphosphane, (S)-(+)-1-[(R)-2-(dicyclohexylphosphano)ferrocenyl]ethyl-dicyclohexylphosphane, (S)-(+)-1-[(R)-2-(dicyclohexylphosphano)ferrocenyl]ethyldiphenyl-phosphane, (R)-(−)-1-[(S)-2-(bis(3,5-dimethyl-4-methoxyphenyl)phosphano)ferrocenyl]-ethyldicyclohexylphosphane, (S)-(+)-1-[(R)-2-(di-furylphosphano)ferrocenyl]ethyldi-3,5-xylyl-phosphane, (R)-(−)-1-[(S)-2-(diphenylphosphano)ferrocenyl]ethyldi-tert-butylphosphane, (S)-(+)-1-[(R)-2-(diphenylphosphano) ferrocenyl]ethyldi-tert-butylphosphane, (R)-(−)-1-[(S)-2-(diphenylphosphano)ferrocenyl] ethyldicyclohexylphosphane, (R)-(+)-1-[(R)-2-(diphenylphosphano)ferrocenyl]ethyldicyclohexylphosphane, (S)-(+)-1-[(R)-2-(diphenylphosphano)-ferrocenyl]

ethyldicyclohexylphosphane, (R)-(−)-1-[(S)-2-(dicyclohexylphosphano)ferrocenyl]-ethyldiphenylphosphane, (R)-(−)-1-[(S)-2-(diphenyl)phosphano)ferrocenyl]ethyldi(3,5-dimethylphenyl)phosphane, (R)-(−)-1-[(S)-2-(di-tert-butyl-phosphano)ferrocenyl]ethyl-di-o-tolylphosphane

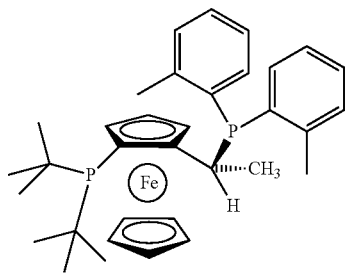

(R)-(−)-1-[(S)-2-(bis(3,5-dimethyl-4-methoxyphenyl)phosphano)ferrocenyl]-ethyl-di-tert-butylphosphane

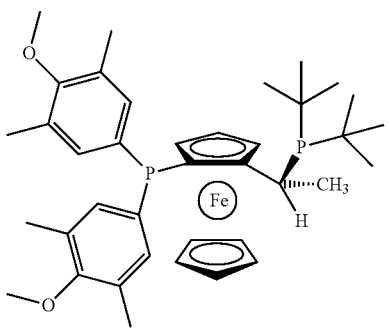

(R)-(−)-1-[(S)-2-(diethylphosphano)ferrocenyl]-ethyl-di-tert-butylphosphane

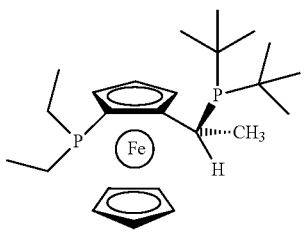

(R)-(−)-1-[(S)-2-(P-methyl-P-isopropyl-phosphano)ferrocenyl]ethyldicyclohexylphosphane

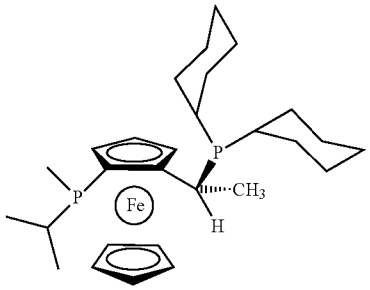

(R)-(−)-1-[(S)-2-(P-methyl-P-phenyl-phosphano)ferrocenyl]ethyl-di-tert-butylphosphane

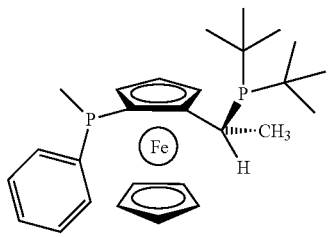

and racemic mixtures thereof, especially racemic mixtures of 1-[2-(di-tert-butylphosphano)-ferrocenyl]ethyl-di-o-tolylphosphane, 1-[2-(dicyclohexylphosphano)ferrocenyl]ethyldi-tert-butylphosphane and 1-[2-(diphenylphosphano)ferrocenyl]ethyldicyclohexylphosphane.

(B1.2) Binaphthyl-bisphosphane Ligands:

2,2'-bis(diphenylphosphano)-1,1'-binaphthyl ("BINAP"), R-(+)-2,2'-bis(di-p-tolylphosphano)-1,1'-binaphthyl ("Tol-BINAP"), racemic 2,2'-bis(di-p-tolylphosphano)-1,1'-binaphthyl ("racemic Tol-BINAP").

(B1.3) 9,9-Dimethyl-4,5-bis(diphenyl-phosphano)-xanthene ("Xantphos").

(B2) Aminophosphane2 ligands:

(B2.1) Biphenyl ligands:

2-dicyclohexylphosphano-(N,N-dimethylamino)-1,1'-biphenyl ("PCy$_2$NMe$_2$BiPh") 2-di-tert-butylphosphano-(N,N-dimethylamino)-1,1'-biphenyl ("P(tBu)$_2$NMe$_2$BiPh").

(C) N-Heterocyclic Carbene Ligands:

1,3-bis-(2,6-diisopropylphenyl)-imidazolium chloride ("I—Pr"), 1,2-bis(1-adamantyl)-imidazolium chloride ("I-Ad") and 1,3-bis-(2,6-methylphenyl)-imidazolium chloride ("I-Me").

(D) Phosphanic acid ligands:

di-tert-butyl-phosphanoxide.

(E) Palladacycles containing a secondary phosphane ligand:

the complex of the formula (A-1)

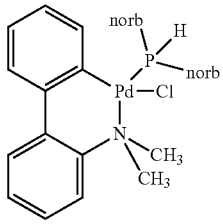

(A-1)

where "norb" is norbornyl, and the complex of the formula (A-2)

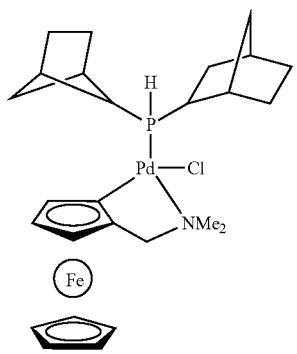

(A-2)

The palladium complex (A-1) is described in Synlett., 2549-2552 (2004) under the code name "SK-CC01-A". The complex (A-2) is described in Synlett. (ibid) under the code name "SK-CC02-A".

Further examples of palladium complexes containing phosphanic acid ligands are described in *J. Org. Chem.* 66, 8677-8681 under the code names "POPd", "POPd2" and "POPD1". Further examples of palladium complexes containing N-heterocyclic carbene ligands are naphthoquinone-1,3-bis(2,6-diisopropylphenyl)imidazole-2-ylidene-palladium (["Pd—NQ-IPr]$_2$"), divinyl-tetramethylsiloxane-1,3-bis(2,6-diisopropylphenyl)imidazole-2-ylidene-palladium ("Pd—VTS-IPr"), 1,3-bis(2,6-diisopropylphenyl)imidazole-2-ylidene-palladium dichloride ("Pd—Cl—IPr"), 1,3-bis(2,6-diisopropylphenyl)imidazole-2-ylidene-palladium diacetate ("Pd—OAc—IPr"), allyl-1,3-bis(2,6-diisopropylphenyl)imidazole-2-ylidene-palladium chloride ("Pd-Al—Cl—IPr") and a compound of the formula (A-3):

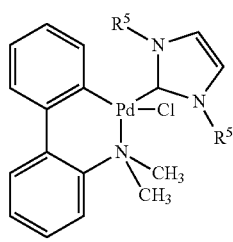

(A-3)

where $R^5$ is 2,6-diisopropylphenyl or 2,4,6-trimethylphenyl. More information about [Pd—NQ-IPr]$_2$, Pd—VTS-IPr, Pd—Cl—IPr, Pd—OAc—IPr and Pd-Al—Cl—IPr can be found in *Organic Letters,* 4, 2229-2231 (2002) and *Synlett.,* 275-278, (2005). More information about the compound of formula (A-3) can be found in *Organic Letters,* 5, 1479-1482 (2003).

A single palladium complex or a mixture of different palladium complexes may be used in the process for preparing the compound of the general formula (VII).

Palladium precursors that are particularly useful for the formation of the palladium complexes are those selected from palladium acetate, palladium$_2$-(dibenzylidene acetone)$_3$, palladium-(dibenzylidene acetone)$_2$, palladium chloride solution or a mixture of palladium$_2$-(dibenzylidene acetone)$_3$ and palladium-(tris-tert.-butylphosphane)$_2$. Palladium acetate is especially useful, as is palladium chloride.

At least one ligand is used for the formation of the palladium complex. Normally the palladium complex will have at least one ligand chosen from a monodentate tertiary phosphane ligand, a bidentate teritary phosphane ligand and a N-heterocyclic carbene ligand, and typically at least one ligand chosen from a ferrocenyl-biphosphane ligand, a binaphthyl-bisphosphane ligand and an aminophosphane ligand.

Particularly suitable are palladium complexes that contain at least one ligand selected from tri-tert-butylphospine, P(tBu)$_3$HBF$_4$, P(oTol)$_3$, P(Cy)$_3$, P(tBu)$_2$BiPh, P(Cy)$_2$BiPh, x-Phos, P(tBu)(Adam)$_2$, (R)-(−)-1-[(S)-2-(dicyclohexylphosphano)ferrocenyl]ethyldi-tert-butyl-phosphane, racemic 1-[2-(dicyclohexylphosphano)ferrocenyl]ethyldi-tert-butylphosphane, (R)-(−)-1-[(S)-2-(di-tert-butyl-phosphano)ferrocenyl]ethyldi-o-tolylphosphane, racemic 1-[2-(di-tert-butyl-phosphano)ferrocenyl]ethyldi-o-tolylphosphane, dppf, 1,1'-bis(di-tert-butyl-phosphano)-ferrocene, (R)-(−)-1-[(S)-2-(diphenylphosphano)ferrocenyl]ethyldicyclohexyl-phosphane, racemic 1-[2-(diphenylphosphano)ferrocenyl]ethyl-dicyclohexylphosphane, (R)-(−)-1-[(S)-2-(diphenylphosphano)ferrocenyl]ethyldi-tert-butylphosphane, BINAP, Tol-BINAP, racemic Tol-BINAP, Xantphos, PCy$_2$NMe$_2$BiPh, P(tBu)$_2$NMe$_2$BiPh, I—Pr, I-Ad and I-Me, and a palladium complex of formula (A-3), where $R^5$ is 2,6-diisopropylphenyl or 2,4,6-trimethyl-phenyl.

Preferred are palladium complexes with at least one ligand selected from tri-tert-butylphospine, P(tBu)$_3$HBF$_4$, P(tBu)$_2$BiPh, P(Cy)$_2$BiPh, x-Phos, (R)-(−)-1-[(S)-2-(dicyclohexylphosphano)ferrocenyl]ethyldi-tert-butylphosphane, racemic 1-[2-(dicyclohexylphosphano)ferrocenyl]ethyldi-tert-butylphosphane, (R)-(−)-1-[(S)-2-(di-tert-butyl-phosphano)ferrocenyl]ethyldi-o-tolylphosphane, racemic 1-[2-(di-tert-butyl-phosphano)ferrocenyl]ethyldi-o-tolylphosphane, dppf, PCy$_2$NMe$_2$BiPh and I—Pr.

Of especial interest are palladium complexes that contain at least one ligand selected from the following groups:

(i) tri-tert-butylphospine, P(tBu)$_3$HBF$_4$, P(tBu)$_2$BiPh, P(Cy)$_2$ BiPh, x-Phos, PCy$_2$NMe$_2$BiPh and I—Pr;

(ii) tri-tert-butylphospine, P(tBu)$_3$HBF$_4$, PCy$_2$NMe$_2$BiPh and I—Pr;

(iii) tri-tert-butylphospine and P(tBu)$_3$HBF$_4$; and (iv) (R)-(−)-1-[(S)-2-(dicyclohexylphosphano)ferrocenyl]ethyldi-tert-butylphosphane and racemic 1-[2-(dicyclohexylphosphano)ferrocenyl]ethyldi-tert-butylphosphane.

Preferred are palladium complexes that contain as a ligand PCy$_2$NMe$_2$BiPh, I—Pr, (R)-(−)-1-[(S)-2-(dicyclohexylphosphano)ferrocenyl]ethyldi-tert-butylphosphane or racemic 1-[2-(dicyclohexylphosphano)ferrocenyl]ethyldi-tert-butylphosphane.

A preferred complex is one where the precursor is palladium chloride and the ligand is (R)-(−)-1-[(S)-2-(dicyclohexylphosphano)ferrocenyl]ethyldi-tert-butylphosphane.

The palladium complex is used in the preparation of the compound of formula (II) in a catalytic amount, normally in a molar ratio of from 1:10 to 1:10000 in respect to the compound of formula (IV), typically in a ratio of 1:100 to 1:1000, for example, 1:500 to 1:700 or about 1:600. The complex may be pre-formed or formed in situ by mixing together the precursor and ligand, which will generally be used in equimolar amounts, or thereabouts.

An especially preferred palladium catalyst for reaction step f) is Pd(OAc)$_2$ (preferred loading is 3-5 mol %, in particular 4 mol %), a ligand selected from the Josiphos, DavePhos (e.g. 2-dicyclohexylphosphano-2'-(N,N-dimethylamino)biphenyl) or Xantphos 4,5-Bis(diphenylphosphano)-9,9-dimethylxanthene) types, preferred is the Josiphos type, in particular Josiphos SL-J009-1 which is (2R)-1-[(1R)-1-[bis(1,1-dimethylethyl)phosphano]ethyl]-2-(dicyclohexylphosphano) ferrocene (preferred amount is 3-5mol %, in particular 4.4 mol %).

NH$_3$ is advantageously added under a pressure of 0.9 to 1.1 MPa, preferably 1 to 1.05 MPa. The reaction step is preferably performed at temperatures from 80 to 150° C., preferably 100 to 120° C. at pressures from 1.4 to 2.6 MPa, preferably 1.5 to 2.2 MPa, in particular 2.2 MPa. Preferred solvents are ethers like dimethylether.

Reaction Step d):

The compound of formula VIII is known and is disclosed, for example, in U.S. Pat. No. 5,093,347. Preferred bases for reaction step d) are amines like triethylamine, or sodium or potassium carbonate or bicarbonate, or NaOH, preferably triethylamine or NaOH.

Preferred solvents are xylene, toluene or chlorobenzene. The reaction is preferably performed at temperatures from −10 to 90° C., preferably from 70 to 80° C.

Reaction Step c2):

The compound of formula VIIIa is for example described in PCT/EP2009/067286. The reaction step c2) can be performed at temperatures from 100 to 180° C., preferably at 130° C. Heating is possible in a sealed vial, open flask, under reflux or under microwave irradiation, preferably in a sealed vial.

As solvents can be used amides (DMF, NMP), alcohols (cyclohexanol), ethers (diglyme, dioxane), sulfoxides (DMSO), hydrocarbons (mesitylene, toluene), nitriles (butyronitrile) and mixtures thereof (toluene/methanol, toluene/cyclohexanol, dioxane/methanol, dioxane/water), preferably toluene and dioxane.

As copper sources can be used Cu(0), Cu(I) or Cu(II) salts. Examples are Cu(0) powder, Cu(I) iodide, Cu(I) thiophenecarboxylate, Cu(II) phthalocyanine, Cu(II) acetate, Cu(II) oxide, Cu(II) chloride, Cu(II) bromide, Cu(II) sulfate pentahydrate and mixtures thereof, preferably Cu(II) oxide and Cu(II) chloride.

The copper catalyst can be used in amounts between 2 and 330 mol-%, preferably 8-12 mol-%, in particular 10 mol-%. If Cu(0) is used, the amount is preferably >100 mol %.

Ligands are generally required for effective catalysis. Examples are N,N'-dimethylethylenediamine, 1,2-bisdimethylaminocyclohexane, 1,2-diaminocyclohexane, 1,2-phenylenediamine, 4-dimethylaminopyridine, 1,2-bis(3-aminopropylamino)ethane, triethylenetetramine, diethylenetriamine, Tris(2-aminoethyl)amine. Preferably, N,N'-dimethylethylenediamine is used. Carbonates can be used as the base, for example cesium carbonate and preferably potassium carbonate. The conversion is generally completed after 5-24 hours.

PREPARATORY EXAMPLES

Step a): Preparation of 5-chloro-9-dichloromethylene-1,4-dihydro-1,4-methano-naphthalene of formula Va

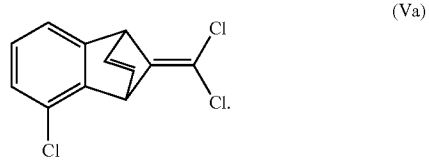 [SMILES: ClC(Cl)=C1C2C=CC1c1c(Cl)cccc12]

A 50% solution of 1,2-dichloro-3-bromobenzene in toluene (45.2 g, 0.10 mol) and 5 minutes delayed in time a 2.7 M solution of nBuLi in heptanes (41 ml, 0.11 mmol) were added over 30 minutes to a 10% solution of dichlorofulvene in toluene (77.3 g, 0.06 mol) at −20° C. The reaction mixture was stirred for an additional hour before a further aliquot of nBuLi (4.1 mL, 0.01 mol) was added and the reaction mixture was stirred for an additional min. Subsequently a third aliquot of nBuLi (4.1 ml, 0.01 mol) was added in order to get complete conversion. After a stirring period of 15 min the reaction mixture was quenched with a sat. aq. NH$_4$Cl solution. The organic layer was extracted twice with water, once with brine and dried over Na$_2$SO$_4$. Yield: 60%.

$^1$H NMR (400 MHz, CDCl$_3$): δ 4.49-4.50 (m, 1H, CH), 4.70-4.71 (m, 1H, CH), 6.90-6.94 (m, 2H, HC=CH), 6.94-7.02 (m, 2H, Ph-H), 7.15 (br d, J(H,H)=8.0 Hz, 1H, Ph-H).

$^{13}$C{$^1$H} NMR (100 MHz, CDCl$_3$): δ 50.9 (CH), 53.0 (CH), 101.0 (C$_{(q)}$Cl$_2$), 120.1 (Ph-H), 126.4 (Ph-H), 127.2 (Ph-H), 127.9 (CCCl$_2$), 141.4 (HC=CH), 142.4 (HC=CH), 145.7 (Ph$_{(q)}$), 149.9 (Ph$_{(q)}$), 159.9 (Ph$_{(q)}$).

The compound 5-bromo-9-dichloromethylene-1,4-dihydro-1,4-methano-naphthalene of formula Vb

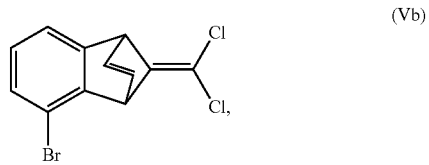

can be prepared analogously.

$^1$H NMR (400 MHz, CDCl$_3$): δ 4.52-4.54 (m, 1H, CH), 4.65-4.66 (m, 1H, CH), 6.90 (dd, J(H,H)=8 Hz, J(H,H)=8 Hz,

1H, Ph-H), 6.91-6.96 (m, 2H, HC=CH), 7.16 (d, J(H,H)=8 Hz, 1H, Ph-H), 7.17 (d, J(H,H)=8 Hz, 1H, Ph-H).

Step b): Preparation of 5-Chloro-9-dichloromethylene-1,2,3,4-tetrahydro-1,4-methano-naphthalene of formula VIa

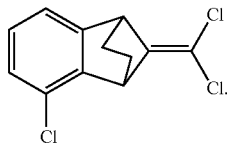

(VIa)

Raney Nickel (1.5 g) was added to a solution of the compound of formula Va (5.4 g, 18.6 mmol) in ethyl acetate (75 ml). The atmosphere above the solution was purged with hydrogen and a balloon filled with hydrogen was placed on top of the reaction vessel. After a stirring period of 4 hours at ambient temperature a further aliquot of Raney Nickel (1.5 g) was added to the reaction solution and it was stirred for 18 hours. The reaction solution was filtered over cellulose. The crude product was purified by column chromatography (hexane). Yield: 74%.

$^1$H NMR (400 MHz, CDCl$_3$): δ 1.30-1.45 (m, 2H, CH$_2$), 2.07-2.15 (m, 2H, CH$_2$), 3.98 (br d, J(H,H)=4 Hz, 1H, CH), 4.19 (br d, J(H,H)=4 Hz, 1H, CH), 7.05-7.15 (m, 3H, Ph-H).

$^{13}$C{$^1$H}NMR (100 MHz, CDCl$_3$): δ 25.5 (CH$_2$), 26.5 (CH$_2$), 45.4 (CH), 47.5 (CH), 104.3 (C$_{(q)}$Cl$_2$), 118.7 (Ph-H), 126.8 (Ph-H), 126.9 (CCCl$_2$), 127.9 (Ph-H), 142.5 (Ph$_{(q)}$), 146.7 (Ph$_{(q)}$), 150.7 (Ph$_{(q)}$).

Step c1): Preparation of 9-dichloromethylene-1,2,3,4-tetrahydro-1,4-methano-naphthalen-5-ylamine of Formula VII Starting from 5-bromo-9-dichloromethylene-1,2,3,4-tetrahydro-1,4-methano-naphthalene

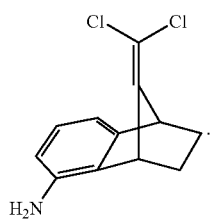

(VII)

Catalyst preparation: 8.98 mg of palladium acetate (0.040 mmol) and 22 mg of Josiphos Ligand (Josiphos SL-J009-1, (2R)-1-[(1R)-1-[bis(1,1-dimethylethyl)phosphano]ethyl]-2-(dicyclohexylphosphano)ferrocene (Solvias AG), 0.040 mmol) were placed in a 5 ml Schlenk tube and inertized with argon/vacuum. 2.5 ml dimethylether was added and the catalyst was left stirring for 15 min.

Starting-Material Solution: 608 mg of 5-bromo-9-dichloromethylene-1,2,3,4-tetrahydro-1,4-methano-naphthalene (2 mmol) was placed in a 5 ml Schlenk tube and inertized with argon/vacuum. 2.5 ml degassed dimethylether was then added to the starting material.

Reaction: 384 mg of NaOtBu (4 mmol) was placed in the stainless steel 50 ml autoclave.

The autoclave was screwed on and set under argon. Under a constant flow of argon, the starting material solution was transferred into the autoclave, followed by the catalyst solution. NH$_3$ was added until pressure reached 1.05 MPa. The autoclave was heated to 105° C., pressure increased to 1.6 MPa. After 32 hour reaction, the reaction was stopped. 79% product was identified by HPLC.

The compound of formula VII can be analogously prepared with 5-chloro-9-dichloromethylene-1,2,3,4-tetrahydro-1,4-methano-naphthalene as starting material.

Step d): Preparation of 3-difluoromethyl-1-methyl-1H-pyrazole-4-carboxylic acid (9-dichloromethylene-1,2,3,4-tetrahydro-1,4-methano-naphthalen-5-yl)-amide of Formula I

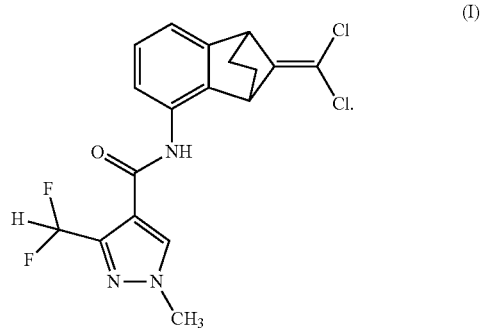 [SMILES: Cn1cc(C(=O)Nc2cccc3c2C2CCC3C2=C(Cl)Cl)c(C(F)F)n1]

(I)

9-Dichloromethylene-1,2,3,4-tetrahydro-1,4-methano-naphthalen-5-ylamine (166 g, 35% xylene solution, 0.25 mol), triethylamine (28 g, 0.275 mol) and xylene (13 g) were charged in a reactor and the mixture was heated to 80° C. 3-Difluoromethyl-1-methyl-1H-pyrazole-4-carbonyl chloride (182 g, 26% xylene solution, 0.25 mol) was added over 2 hours. After conversion, the product was extracted, concentrated and crystallized in a mixture of xylene/methycyclohexane. 83 g of pure product were isolated. (Purity: 97%, Yield: 82%) $^1$H-NMR (400 MHz, CDCl$_3$): δ=8.12 (bs, 1H, NH); 8.05 (s, 1H, Pyr-H); 7.83-7.80 (d, 1H, Ar—H); 7.19-7.15 (t, 1H, Ar—H); 7.04 (d, 1H, Ar—H); 7.02-6.76 (t, 1H, CHF$_2$); 4.1 (s, 1H, CH); 3.95-4.0 (bs, 4H, CH & CH$_3$); 2.18-2.08 (m, 2H, CH$_2$); 1.55-1.3 (2m, 2H, CH$_2$).

Step c2): Preparation of 3-difluoromethyl-1-methyl-1H-pyrazole-4-carboxylic acid (9-dichloromethylene-1,2,3,4-tetrahydro-1,4-methano-naphthalen-5-yl)-amide of Formula I A 20 ml screw-cap vial was filled with the following solids: CuO (0.05 mmol, 4.0 mg), anhydrous CuCl$_2$ (0.05 mmol, 6.7 mg), K$_2$CO$_3$ (2.0 mmol, 277 mg), 3-difluoromethyl-1-methyl-1H-pyrazole-4-carboxylic acid amide (1.1 mmol, 193 mg) and 5-bromo-9-dichloromethylene-1,2,3,4-tetrahydro-1,4-methano-naphthalene (1.0 mmol, 304 mg). A magnetic stir bar was added, and the open vial was gently flushed with N$_2$. Dioxane (2 mL) was added, followed by N,N'-dimethylethylenediamine (0.45 mmol, 48 µl). The vial was sealed and placed into a preheated screening block at 130° C. Conversion was complete after 24 hours. The yield (HPLC-analysis) of the compound of formula I was 70%.

The reaction can be performed analogously using 5,9,9-trichloromethylene-1,2,3,4-tetrahydro-1,4-methano-naphthalene as starting material.

What is claimed is:

1. A process for the preparation of the compound of formula I

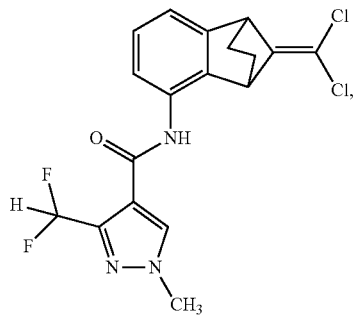

(I)

which process comprises a) reacting a compound of formula II

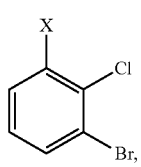

(II)

wherein X is chloro or bromo, with an organometallic species in an inert atmosphere to a halobenzyne of formula III

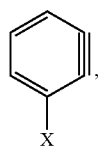

(III)

wherein X is chloro or bromo; reacting the halobenzyne of formula III so formed with a fulvene of formula IV

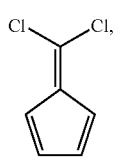

(IV)

to a compound of formula V

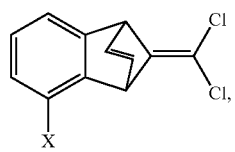

(V)

wherein X is chloro or bromo;

b) hydrogenating the compound of formula V in the presence of a suitable metal catalyst to a compound of formula VI

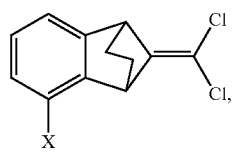

(VI)

wherein X is chloro or bromo; and either c1) reacting the compound of formula VI with $NH_3$ in the presence of a catalyst comprising palladium and at least one ligand to the compound of formula VII

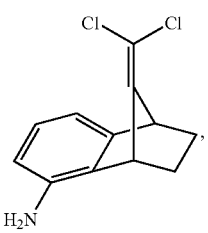

(VII)

and d) reacting the compound of formula VII in the presence of a base with a compound of formula VIII

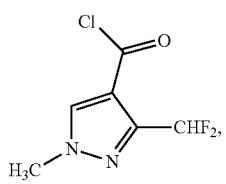

(VIII)

to the compound of formula I; or c2) reacting the compound of formula VI

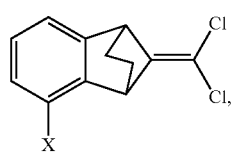

(VI)

wherein X is chloro or bromo; in the presence of a solvent, a base, a copper catalyst and at least one ligand with the compound of formula VIIIa

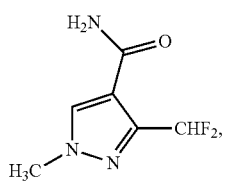
(VIIIa)

to the compound of formula I.

2. A process according to claim 1, wherein in step a) the organometallic species is selected from $C_{1-6}$ alkyl- or phenyllithium halides and $C_{1-6}$ alkyl- or phenylmagnesium halides.

3. A process according to claim 1, wherein in step c) the ligand is selected from ferrocenyl-biphosphane ligands.

4. A process according to claim 1, which comprises reacting the compound of formula VI with $NH_3$ in the presence of a catalyst comprising palladium and at least one ligand to the compound of formula VIII (VII)

and reacting the compound of formula VII in the presence of a base with a compound of formula VIII (VIII)

to the compound of formula I.

5. The compound of formula V (V)

wherein X is chloro or bromo.